United States Patent
Prencipe et al.

(10) Patent No.: US 8,485,821 B2
(45) Date of Patent: *Jul. 16, 2013

(54) TOOTH WHITENING DENTAL TRAY AND METHOD OF USE

(75) Inventors: Michael Prencipe, West Windsor, NJ (US); Suman K. Chopra, Dayton, NJ (US); Michael Collins, Hazlet, NJ (US)

(73) Assignee: Colgate-Palmolive Company, New York, NY (US)

( * ) Notice: Subject to any disclaimer, the term of this patent is extended or adjusted under 35 U.S.C. 154(b) by 1455 days.

This patent is subject to a terminal disclaimer.

(21) Appl. No.: 12/105,065

(22) Filed: Apr. 17, 2008

(65) Prior Publication Data

US 2008/0213730 A1 Sep. 4, 2008

Related U.S. Application Data

(63) Continuation of application No. 10/754,065, filed on Jan. 7, 2004, now abandoned, which is a continuation-in-part of application No. 10/642,458, filed on Aug. 15, 2003, now abandoned.

(51) Int. Cl.
  *A61K 6/00* (2006.01)
  *A61K 8/22* (2006.01)
  *A61K 8/25* (2006.01)
  *A61Q 11/00* (2006.01)

(52) U.S. Cl.
  USPC ........... 433/216; 424/401; 424/613; 424/616; 424/53; 433/217.1

(58) Field of Classification Search
  USPC .................... 424/53, 401, 613, 616; 433/216, 433/217.1
  See application file for complete search history.

(56) References Cited

U.S. PATENT DOCUMENTS

| | | | |
|---|---|---|---|
| 3,215,599 A | 11/1965 | Thau et al. |
| 3,339,547 A | 9/1967 | Drabkowski |
| 3,376,110 A | 4/1968 | Shiraeff |
| 3,379,193 A | 4/1968 | Monaghan |
| 3,480,557 A | 11/1969 | Shiraeff |
| 3,688,406 A | 9/1972 | Porter et al. |
| 4,514,528 A | 4/1985 | Dhabhar et al. |
| 4,569,955 A | 2/1986 | Dhabhar |
| 4,582,701 A | 4/1986 | Piechota, Jr. |
| 4,585,836 A | 4/1986 | Homan et al. |
| 4,713,243 A | 12/1987 | Schiraldi et al. |
| 4,948,580 A | 8/1990 | Browning |
| 5,059,189 A | 10/1991 | Cilento et al. |
| 5,122,370 A | 6/1992 | Merianos et al. |
| 5,232,702 A | 8/1993 | Pfister et al. |
| 5,310,563 A | 5/1994 | Curtis et al. |
| 5,656,286 A | 8/1997 | Miranda et al. |
| 5,676,932 A | 10/1997 | Wason et al. |
| 5,707,611 A | 1/1998 | Ikemura et al. |
| 5,846,058 A | 12/1998 | Fischer |
| 6,089,869 A | 7/2000 | Schwartz |
| 6,306,370 B1 | 10/2001 | Jensen et al. |
| 6,419,906 B1 | 7/2002 | Xu et al. |
| 6,514,484 B2 | 2/2003 | Rajaiah et al. |
| 6,565,969 B1 | 5/2003 | Lamon et al. |
| 6,740,311 B2 | 5/2004 | White, Jr. et al. |
| 6,860,736 B2 | 3/2005 | Allred et al. |
| 2002/0137728 A1 | 9/2002 | Montgomery |
| 2002/0141950 A1 | 10/2002 | Chen |
| 2002/0187108 A1 | 12/2002 | Rajaiah et al. |
| 2003/0129148 A1 | 7/2003 | Chen |
| 2003/0194382 A1 | 10/2003 | Chang et al. |
| 2004/0219190 A1 | 11/2004 | Kosti |
| 2007/0122357 A1 | 5/2007 | Glandorf |

FOREIGN PATENT DOCUMENTS

| | | |
|---|---|---|
| EP | 0325267 | 5/1994 |
| WO | WO 99/62472 | 12/1999 |
| WO | WO 01/01939 | 1/2001 |
| WO | WO 01/01942 | 1/2001 |
| WO | WO 01/01958 | 1/2001 |
| WO | WO 01/76549 | 10/2001 |
| WO | WO 01/85116 | 11/2001 |
| WO | WO 02/34221 | 5/2002 |
| WO | WO 02/43657 | 6/2002 |
| WO | WO 02/074274 | 9/2002 |
| WO | WO 03/094877 | 11/2003 |

*Primary Examiner* — Lezah Roberts
(74) *Attorney, Agent, or Firm* — Nikhil A. Heble

(57) ABSTRACT

A dental tray with a hydrophobic tooth whitening formulation where the tooth whitening formulation is substantially non-water soluble, and a method of using this dental tray to whiten the teeth. The tooth whitening formulation is primarily comprised of a hydrophobic polymer and a peroxide or a peroxide yielding compound. Preferably the hydrophobic polymer is the condensation product of a silicone resin and an organosiloxane. The dental tray is formed to encompass the front and the rear surfaces of the teeth. The dental tray is comprised of a thermoplastic or thermoset polymer. The teeth whitening formulation is placed into the dental tray and the tray placed against the teeth to be whitened. This is for a sufficient period of time to at least partially whiten teeth. This can be a period of time from about 0.5 hour to 2 hours or more. The substantially non-aqueous tooth whitening formulation is effective over a longer period of time since it is not significantly diluted or removed from the dental tray during the treatment time.

9 Claims, No Drawings

TOOTH WHITENING DENTAL TRAY AND METHOD OF USE

CROSS REFERENCE TO RELATED APPLICATIONS

This application is a continuation of U.S. patent application Ser. No. 10/754,065, filed Jan. 7, 2004 (abandoned), which is a continuation-in-part of U.S. patent application Ser. No. 10/642,458, Filed on Aug. 15, 2003, the contents of which are herein incorporated by reference.

This invention relates to a dental tray and formulation for tooth whitening. More particularly this invention relates to a substantially non-water soluble tooth whitening formulation in a dental try and its use for tooth whitening.

BACKGROUND OF THE INVENTION

There is a general desire for people to have white teeth. Such white teeth are an indication of good health and in particular good oral care health. A problem is that various foods and the use of tobacco will discolor teeth. Beverages such as coffee, tea and cola beverages can discolor teeth.

As a result various products and procedures have been developed to whiten teeth. These products and procedures are either purchased and/or used directly by the consumer or are applied by a dentist or other professional. The more effective products and procedures are those that are performed by a dental professional.

Typically this consists of the dental professional forming a dental tray from an impression of a person's teeth. The dental tray is formed by any of the well known and well used procedures. After the dental tray is formed to the structure of the teeth a whitening formulation is placed in the tray and the tray placed into the mouth and against the teeth to be treated. The tray with the whitening composition in home use typically is left in the mouth for from about 10 minutes to several hours; i.e. up to 12 or more hours. If the treatment is only in the dental office the time of the treatment typically will be from about 0.5 hour to about 2 hours.

The products used solely by consumers primarily comprise whitening strips and brush-on products. Whitening strips are plastic strips with the whitening formulation on one surface. The surface with the whitening formulation is pressed against one's teeth and left in contact with the teeth for about 30 minutes. The plastic strip then is removed. The brush-on products are painted onto teeth and the user keeps his/her mouth at least partially open for up to about a minute until the formulation dries onto the teeth. In both cases saliva will dilute and flush the tooth whitening composition from the user's teeth. This is more so with strips since foreign materials, such as a plastic strip, will enhance saliva flow in the mouth. These are useful products to remove some tooth staining. However, they are not as effective as the use of dental trays, and in particular the use of dental trays by dental professionals.

A problem with the various whitening compositions that are used in dental trays is that they are substantially soluble in water and saliva. This results in a dilution of the whitening formulation during use. In order to overcome this problem producers of these whitening formulations have increased the concentration of the whitening actives. However, this causes a problem of increased tooth sensitivity, gum irritation and the potential long term for lesions. Another solution disclosed in U.S. Pat. No. 5,846,058 has been to use higher viscosity tooth whitening compositions. This increases dilution time and flush time but is not a full solution to the problem. A better solution to this problem is to use a carrier and actives that are substantially insoluble in water and saliva, the carrier being about fully insoluble in water and saliva. The active must have some solubility in order to attack and remove tooth stains. However this should be at a low level. In this way tooth whitening compositions with a lower concentration of active can be used to enhance whitening through a longer contact time at a more sustained active concentration.

BRIEF DESCRIPTION OF THE INVENTION

The dental tray can be formed from essentially any thermoplastic or thermoset polymer. The only requirement is that preferably it should be at least partially flexible to better fit into the mouth and against the teeth to be treated with the tooth whitening composition. The tooth whitening composition to be placed into the dental tray will be a substantially non-water and non-saliva soluble composition. The major components of this tooth whitening composition will comprise a non-aqueous hydrophobic polymer and a peroxide whitening agent; and optionally components such as an adhesive enhancing agent, surfactant, flavor and peroxide activator. Other optional materials such as substances with antiseptic and medicinal properties also can be a part of the tooth whitening composition. This tooth whitening composition will have a viscosity of about 50,000 cps to about 900,000 cps, and preferably about 200,000 cps to about 600,000 cps.

This tooth whitening composition is placed in the dental tray and the dental tray applied to the teeth to be treated. The tray is left in place for about 0.25 hour to about 4 hours and preferably from about 0.5 hour to about 2 hours. After removal the person may rinse his/her mouth.

After the treatment with the tooth whitening composition the teeth can be treated with a tooth desensitizing formulation. This can be via use of the tray for more severe conditions to the use of a desensitizing toothpaste for several days. Such formulations will contain potassium nitrate, citric acid, citric acid salts, strontium chloride and the like. A process of a first step tooth whitening procedure followed by a tooth desensitizing procedure is preferred for persons who are susceptible to tooth sensitivity problems.

DETAILED DESCRIPTION OF THE INVENTION

The present invention will be described in more detail with reference to the preferred embodiments. However, modifications can be made to these preferred embodiments and be within the disclosed concept.

The dental tray can be of any conventional form and formed from conventionally used thermoplastic polymers. Thermoset polymers also can be used. Consequently the tray can range from highly flexible to a low flexibility. The thermoplastic polymers are highly preferred and those that can be used include polyethylene and polypropylene polymers their derivatives and copolymers, silicone elastomers, polyurethanes and derivatives, polycaprolactams, polystyrene and derivatives, polybutadiene and derivatives, polyisoprene and derivatives, and polymethacrylate and its derivatives. These can be in a sheet, foam or a laminate form. In forming the trays a cast is taken of the teeth and gum area of a patient and set. A thermoplastic polymer film is placed over the cast and vacuum formed to the shape of the teeth and gum margin of the patient. This is now in the shape of a tray that can contain a whitening formulation and be used to treat the patients teeth.

The term "hydrophobic" polymer or "water-insoluble" polymers as employed herein refers to an organic polymer which is substantially non-aqueous having a water solubility of less than one gram per 100 grams of water at 25 C. Any such polymers that are compatible with peroxide compounds or peroxide yielding compounds and which can produce a tooth whitening composition having a viscosity of about 1000 cps to about 900,000 cps, and preferably about 10,000 cps to about 100,000 cps can be used.

The composition of the present invention is a viscous suspension which maintains its consistency during storage enabling the product to be painted on the tooth surface through the use of a dental tray. The composition is comprised of a hydrophobic polymer that is the primary carrier for the active whitening component which preferably is a peroxide containing or peroxide yielding compound. A preferred class of hydrophobic polymers are silicone based polymers. There are other components such as adhesion enhancing agents, flavors, sweetening agents, surfactants, anti-microbial agents, anti-inflammatory agents, plaque buffers, vitamins, anti-caries agents, anti-plaque agents, desensitizing agents, coloring agents, pigments and opacifying agents.

The tooth whitening composition will have the following general formula:

| Component | Content |
| --- | --- |
| Hydrophobic Polymer | 1 to 80 wt % |
| Adhesive Enhancing Agent | 0 to 20 wt % |
| Peroxide Whitening Agent | 0.5 to 50 wt % |
| Surfactant | 0 to 50 wt % |
| Flavor | 0.1 to 1 wt % |
| Other Components (can be HOH) | 0 to 10 wt % |

In accordance with the practice of the present invention the hydrophobic polymer compositions in which a peroxide can be dispersed are known in the art and many are commercially available. The preferred silicone based hydrophobic polymers are produced by condensing a silicone resin and an organosiloxane such as a polydiorganosiloxane. The hydrophobic polymers are an elastomeric, tacky material, adhesion of which to dental enamel surfaces can be varied by altering the ratio of silicone resin to polydiorganosiloxane in the copolymer molecule. For example hydrophobic polymers available from the Dow-Corning Company under the brand name BIO-PSA are pressure sensitive hydrophobic polymers specifically designed for pharmaceutical use and are permeable to many drug compounds and find application for the transdermal application of various compounds. The BIO-PSA silicone polymers are the copolymer product of mixing a silanol terminated polydiorganosiloxane such as polydimethyl siloxane with a silanol-containing silicone resin whereby the silanol groups of the polydiorganosiloxane undergo a condensation reaction with the silanol groups of the silicone resin so that the polydiorganosiloxane is lightly crosslinked by the silicone resin (that is, the polydiorganosiloxane chains are bonded together through the resin molecules to give chain branching and entanglement and/or a small amount of network character) to form the silicone hydrophobic polymers. A catalyst, for example an alkaline material such as ammonia, ammonium hydroxide or ammonium carbonate can be mixed with the silanol-terminated polydiorganosiloxane and the silicone resin to promote this crosslinking reaction.

By copolymerizing the silicone resin with the silanol terminated polydiorganosiloxane, there results a polymer with self adhering properties and the cohesive properties of a soft elastomer matrix characteristic of pressure sensitive polymers being distinguished from the hard, non-elastomeric properties of other silicone resins.

Modifying the silicone resin to polydiorganosiloxane ratio will modify the tackiness of the hydrophilic polymer. This ratio can be in the range of about 70:30 to about 50:50. For example, the BIO PSA silicone sold by Dow-Corning is available in three silicone resin to silicone polymer ratios namely, 65/35 (low tack), 60/40 (medium tack), 55/45 (high tack). This is available dissolved in either ethyl acetate solvent or dimethicone.

The silicone based hydrophobic polymer is present in the liquid whitening compositions of the present invention at a concentration of about 1 to about 80% by weight and preferably about 15 to about 40% by weight.

Organic materials which may be included in the compositions of the present invention to enhance the properties of the hydrophobic polymers of the present invention include adhesion enhancing agents such as waxes inclusive of bees wax, mineral oil, plastigel, (a blend of mineral oil and polyethylene), petrolatum, white petrolatum, shellac, versagel (blend of liquid paraffin, butene/ethylene/styrene hydrogenated copolymer) polyethylene waxes, microcrystalline waxes, polyisobutene, polyvinyl pyrrolidone/vinyl acetate copolymers, and insoluble polyacrylate copolymers. Also effective as adhesion enhancing agents are liquid hydrophilic polymers including polyethylene glycols, nonionic polymers of ethylene oxide having the general formula:

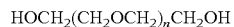

wherein n represents the average number of oxyethylene groups. Polyethylene glycols available from Dow Chemical are designated by a number such as 200, 300, 400, 600, 2000 which represents the approximate average molecular weight of the polymer, as well as nonionic block copolymer of ethylene oxide and propylene oxide of the formula:

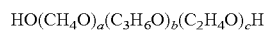

The block copolymer is preferably chosen (with respect to a, b and c) such that the ethylene oxide constituent comprises from about 65 to about 75% by weight, of said copolymer molecule and the copolymer has an average molecular weight of from about 2,000 to about 15,000 with the copolymer being present in the liquid tooth whitening composition in such concentration that the composition is liquid at room temperatures (23° C.).

A particularly desirable block copolymer for use in the practice of the present invention is available commercially from BASF and designated Pluraflo L1220 which has an average molecular weight of about 9,800. The hydrophilic poly(ethylene oxide) block averages about 65% by weight of the polymer.

Typically, adhesion enhancing polymers employed in the compositions of the invention are present in an amount of from about 0 to 20% by weight. Preferably, the polymers are present in an amount of from about 2 to about 15% by weight.

Peroxide releasing compounds useful in the practice of the present invention include peroxide containing compounds such as urea peroxide, sodium percarbonate, sodium perborate and PVP-H$_2$O$_2$ complexes (hereinafter "PVP-H$_2$O$_2$"). PVP-H$_2$O$_2$ both linear and cross linked complexes are known to the art and are disclosed in U.S. Pat. No. 3,376,110 and U.S. Pat. No. 3,480,557 and have been used in compositions for treating acne vulgaris (U.S. Pat. No. 5,122,370). PVP-H$_2$O$_2$ complexes are disclosed in U.S. Pat. No. 5,122,370. PVP-H$_2$O$_2$ is stable in an anhydrous environment. By exposure to aqueous environments, as in the oral cavity, the PVP-H$_2$O$_2$ dissociates into individual species (PVP polymer and H$_2$O$_2$).

The PVP-H$_2$O$_2$ complex is generally comprised of about 80% by weight polyvinyl pyrrolidone and 20% by weight H$_2$O$_2$. It also may be useful to have as a part of the peroxide component an agent to enhance the release of peroxide. Polypore® which is an allyl methacrylate crosspolymer available from Amcol health & Beauty Solutions, Inc. is such an enhancing agent.

The peroxide releasing compound is present in the liquid whitening compositions of the present invention at a concentration of about 0.5 to about 50% by weight and preferably about 10 to about 40% by weight.

Nonionic surfactants which are compatible with peroxide compounds serve as solubilizing, dispersing, emulsifying and wetting agents and are especially effective to solubilize a flavor if included in the liquid whitening composition. A particularly useful nonionic surfactant is a water soluble polyoxyethylene monoester of sorbitol with a C10 to C18 fatty acid, marketed commercial under the Tween trademark. The Tween surfactants are mixtures of C10 to C18 fatty acid esters of sorbitol (and sorbitol anhydrides), consisting predominately of the monoester, condensed with about 10-30, preferably about 20, moles of ethyleneoxide. The fatty acid (aliphatic hydrocarbonyl monocarboxylic acid) may be saturated or unsaturated, e.g., lauric, palmitic, stearic, oleic acids. Polysorbate 20 (e.g., Tween 20) is especially preferred and is commonly referred to as polyoxyethylene (20) sorbitan monolaurate. The nonionic surfactant constitutes about 0 to 50% by weight and preferably 0.5 to 40% by weight of the liquid composition.

The liquid whitening composition of the present invention may also contain a flavoring agent. Flavoring agents that are used in the practice of the present invention include essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Of these, the most commonly employed are the oils of peppermint, spearmint and wintergreen. The flavoring agent is incorporated in the whitening liquid composition of the present invention at a concentration of about 0.0 to about 2% by weight and preferably about 0.1 to about 0.5% by weight.

A sweetening material may also be employed as an alternative or complement to the flavoring material. Suitable sweetening agents are water soluble and include sodium saccharin, sodium cyclamate, xylitol, perillartien, D-tryptophan, aspartame, dihydrochalcones and the like, in concentrations of about 0.01 to about 1% by weight. Sodium saccharin is preferred.

Other ingredients which are included in the liquid whitening composition comprise materials commonly used in the oral care formulations. These include: antimicrobial agents, e.g., Triclosan, chlorhexidine, copper-, zinc- and stannous salts such as zinc citrate, zinc sulphate, zinc glycinate, sodium zinc citrate and stannous pyrophosphate, sanguinarine extract, metronidazole, quaternary ammonium compounds, such as cetylpyridinium chloride; bis-guanides, such as chlorhexidine digluconate, hexetidine, octenidine, alexidine; and halogenated bisphenolic compounds, such as 2,2' methylenebis-(4-chloro-6-bromophenol); antiinflammatory agents such as ibuprofen, flurbiprofen, aspirin, indomethacine; anticaries agents such as sodium-, calcium-, magnesium- and stannous fluoride, aminefluorides, disodium monofluorophosphate and sodium trimetaphosphate; plaque buffers such as urea, calcium lactate, calcium glycerophosphate and strontium polyacrylates; vitamins such as Vitamin C; plant extracts; desensitizing agents, e.g., potassium citrate, potassium chloride, potassium tartrate, potassium bicarbonate, potassium oxalate, potassium nitrate and strontium salts; agents effective against dental calculus such as pyrophosphate salts including the mono, di, tri and tetra alkali metal and ammonium pyrophosphate and tripolyphosphate salts; biomolecules, e.g., bacteriocins, antibodies, enzymes such as papain, glucoamylase; opacifying agents, pigments, coloring agents and fluoride ion providing salts having anticaries efficacy such as sodium fluoride, potassium fluoride, a tin fluoride such as stannous fluoride.

The liquid whitening compositions of the present invention are prepared by adding and mixing the ingredients of the composition in a suitable vessel such as a stainless steel tank provided with a mixer. In the preparation of the liquid whitening composition, the ingredients are advantageously added to the mixer in the following order: liquid anhydrous silicone based pressure sensitive polymer, peroxide whitening agent, adhesion enhancing agent and any desired flavoring or sweetener. The ingredients are then mixed to form a homogeneous dispersion/solution. The moisture content of the tooth whitening composition will be about 0.05% by weight to about 10% by weight, and preferably about 2% by weight to about 8% by weight. The viscosity will be about 50,000 cps to about 900,000 cps and preferably about 200,000 cps to about 600,000 cps.

The present invention is illustrated by the following examples but is not to be limited thereby.

Examples 1-4

The formulations in the following Table 1 were formed by adding the silicone hydrophobic polymers Dow Corning Q7-9120 and Dow Corning 8-7016 in a dimethicone solvent to a Brogli mixer. These two components were mixed for 30 minutes at high speed without vacuum. Sodium saccharin was added and mixing continued for 3 minutes at high speed without vacuum. The COP Plastigel 5 was then added and mixing continued for 10 minutes at high speed without vacuum. The Polyplasdoxyl XL10, 35% hydrogen peroxide peralkali and flavor were added and mixed on a low speed without vacuum for 5 minutes. Full vacuum then is applied and the formulation is mixed at high speed for an additional 15 minutes.

TABLE 1

| Ingredient | Example 1 (Wt. %) | Example 2 (Wt. %) | Example 3 (Wt. %) | Example 4 (Wt. %) |
| --- | --- | --- | --- | --- |
| Dow Corning 8-7016 | 30.0 | 30.0 | 30.0 | 30.0 |
| Dow Corning Q7-9120 | 20.0 | 16.46 | — | 20.0 |
| Plunacare L 1220 | — | — | — | 0.05 |
| Polyplasdone XL-10 | 25.0 | 25.0 | 25.0 | 25.0 |
| COP Plastigel 5 (Lyne Labs) | 20.1 | 15.5 | | 11.91 |
| 35% Hydrogen Peroxide Peralkali | 4.0 | 12.14 | 44.1 | 12.14 |
| Sodium Saccharin | 0.3 | 0.3 | 0.30 | 0.30 |
| VW Mint Flavor | 0.6 | 0.6 | 0.6 | 0.60 |
| Viscosity cps | 180,000 | 180,000 | 270,000 | 360,000 |

The formulations of Examples 1-4 have viscosities of 180,000 cps to 360,000 cps. These formulations were found to have a workable consistency in being applied to a tray and in adherence to teeth. There also is a low loss of formulation from the tray by the natural flushing action of saliva.

Example 5

The formulation of Example 3 was tested in vitro against a hydrophilic commercial tooth whitening product. Six naturally stained prophied human teeth were placed into two preformed thermoplastic trays, custom fitted to the teeth. In one tray was the formulation of Example 3 along with 3 ml of saliva and in the other tray was the commercial product and 3 ml of saliva. The saliva is added to replicate mouth conditions. The formulation of Example 3 and the commercial product were tested. The Example 3 formulation and the commercial product were placed in separate trays with the teeth for a period of 1 hour. There were 2 applications of the formulation and the product to the teeth. After each 1 hour period the teeth were rinsed with deionized water and maintained in contact with deionized water. There was a period of 10 minutes between each treatment.

Table 2 gives the data from statistical analysis of the bleach action on the test teeth as noted by the color change after 2 treatments for 1 hour each. The tests were conducted on a Minolta CR-321 chromometer based on initial L, a and b CIELAB values. The L, a and b values were measured four times at differing locations on the surface of the teeth. The average initial and the final chromometer were used to calculate delta E according to (formula). The final delta E was the average over all observations after the rejection of outliers using the Students test (95% confidence level). The product of Example 3 produces the greater color change to the teeth.

TABLE 2

Color Change after 5 Treatments (15 hours)

| Product | ΔL | Δb | ΔE |
|---|---|---|---|
| Commercial | 4.0 | −4.4 | 6.4 |
| Example 3 | 6.1 | −7.0 | 9.5 |

Table 3 shows the consumption of peroxide during a 3 hours test. The commercial aqueous hydrophilic product consumed 26.7% of the peroxide while the hydrophilic product of Example 3 consumed only 8.9% of the peroxide.

TABLE 3

% Peroxide consumption after 3 hours

| Product | Initial HP Concentration (%) | *Final HP Concentration (%) | % HP Consumed |
|---|---|---|---|
| Commercial | 3 | 2.2 | 26.7 |
| Example 3 | 4.5 | 4.1 | 8.9 |

The net result is that the hydrophilic formulation consumes less peroxide to yield more stain removal. If treatments are continued for more than 3 hours there will be more peroxide available (higher concentration) to remove stains and to whiten teeth.

The invention claimed is:

1. A dental tray for treating teeth with a whitening formulation comprising a dental tray formed to cover the front and a rear surface of at least one tooth, said dental tray containing a non-water soluble whitening formulation having a viscosity of about 50,000 cps to about 900,000 cps comprising a hydrophobic polymer that is a condensation product of a silicone resin and an organosiloxane, wherein the polymer is comprised of about 50 to 70 parts silicone resin to 30 to 50 parts organosiloxane polymer.

2. A dental tray as in claim 1 wherein said non-water soluble whitening formulation has a viscosity of about 200,000 cps to about 600,000 cps.

3. A dental tray as in claim 1 wherein said non-water soluble whitening formulation has the following formula:

| Component | Content |
|---|---|
| Hydrophobic Polymer | 1 to 80 wt % |
| Adhesive Enhancing Agent | 0 to 20 wt % |
| Peroxide Whitening Agent | 0.5 to 50 wt % |
| Surfactant | 0 to 50 wt % |
| Flavor | 0.1 to 1 wt % |
| Other Agents | 0 to 10 wt %. |

4. A dental tray as in claim 3, wherein said hydrophobic polymer has a concentration of about 15 to about 40 weight %.

5. A dental tray as in claim 3, wherein said adhesive enhancing agent has a concentration of about 2 to 15 weight %.

6. A dental tray as in claim 3, wherein said peroxide whitening agent has a concentration of about 10 to 40 weight %.

7. A dental tray as in claim 3, wherein said peroxide whitening agent has a concentration of about 15 to about 35 weight %.

8. A dental tray as in claim 1, wherein the hydrophobic polymer is selected from a condensation product comprised of 65 parts silicone resin and 35 parts organosiloxane polymer; a condensation product comprised of 60 parts silicone resin and 40 parts organosiloxane polymer; and a condensation product comprised of 55 parts silicone resin and 45 parts organosiloxane polymer.

9. A dental tray as in claim 3, wherein said adhesive enhancing agent is selected from the group consisting of a wax, a nonionic polymer of ethylene oxide, and a nonionic copolymer of ethylene oxide and propylene oxide.

* * * * *